United States Patent [19]
Fettel et al.

[11] 4,276,132
[45] Jun. 30, 1981

[54] ELECTRO-CHEMICALLY MACHINED RING AND STRUT STRUCTURE FOR PROSTHETIC HEART VALVES

[75] Inventors: Bruce E. Fettel, Newport Beach; Paul E. Morris, Mission Viejo; Leo J. Lichte, Riverside, all of Calif.

[73] Assignee: Shiley Incorporated, Irvine, Calif.

[21] Appl. No.: 18,566

[22] Filed: Mar. 8, 1979

Related U.S. Application Data

[63] Continuation-in-part of Ser. No. 870,685, Jan. 19, 1978, abandoned.

[51] Int. Cl.³ .......................... B23P 1/00; A61F 1/22
[52] U.S. Cl. ............................ 204/129.1; 204/129.6; 204/224 M; 3/1.5
[58] Field of Search ............ 204/129.1, 129.6, 224 M; 3/1.5; 137/533.27

[56] References Cited

U.S. PATENT DOCUMENTS

| | | | |
|---|---|---|---|
| 3,503,079 | 3/1970 | Smith | 3/1.5 |
| 3,534,411 | 10/1970 | Shiley | 3/1.5 |
| 3,689,942 | 9/1972 | Rapp | 3/1.5 |
| 3,694,610 | 9/1972 | Saito et al. | 204/129.1 X |
| 3,812,542 | 5/1974 | Shiley | 137/533.27 X |
| 4,021,863 | 5/1977 | Wøien | 3/1.5 |
| 4,038,702 | 8/1977 | Sawyer | 204/129.1 X |
| 4,057,857 | 11/1977 | Fettel | 3/1.5 |
| 4,184,254 | 1/1980 | Kraus | 204/129.6 X |

FOREIGN PATENT DOCUMENTS 930328 7/1973 Canada .................. 204/129.1
2229483 1/1974 Fed. Rep. of Germany ........ 204/129.1

*Primary Examiner*—Donald R. Valentine
*Attorney, Agent, or Firm*—Knobbe, Martens, Olson, Hubbard & Bear

[57] ABSTRACT

This invention relates to the electrochemical machining of integrally formed prosthetic heart valve structures in which both the structural integrity of the valve and the blood flow through the valve is improved as a result of the integral formation of the valve structure. In particular, such heart valves comprise a ring and a pendant structure, such as a strut, for supporting the opening and closing of a discoid valve occluder. Integral formation of the strut with the ring permits the cross-sectional shape of the strut to be machined without overheating and distortion to conform to a teardrop shape having favorable fluid-dynamic characteristics thereby improving the flow of blood through the valve across the strut. The integral formation of the strut with the ring further results in the elimination of the weld fillet between the strut and the ring, thereby permitting the height of the ring to be reduced, which further improves the fluid dynamic characteristics of the valve. The overall structural integrity of the heart valve structure is also improved by the shape of the strut which permits the increase in the total cross-sectional area of the strut while retaining the favorable fluid flow characteristics of the valve. Thus, this invention provides for improved structural integrity of the valve and at the same time, improved flow characteristics through the valve.

11 Claims, 31 Drawing Figures

FIG. 3
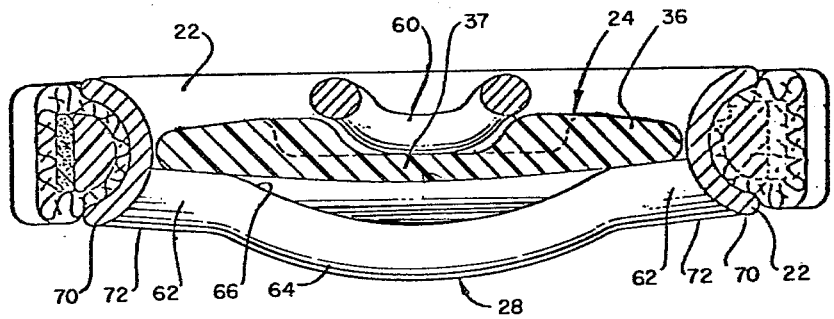
FIG. 4
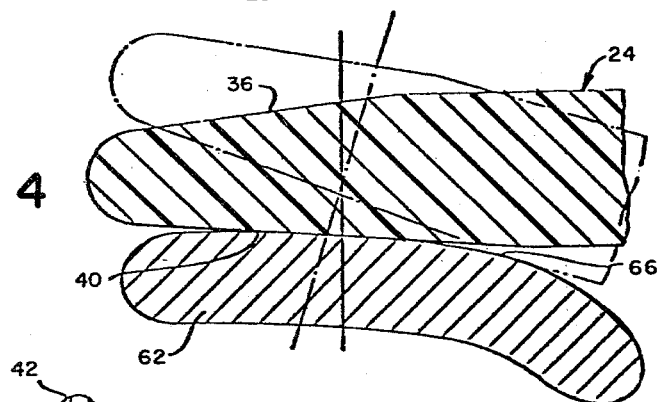
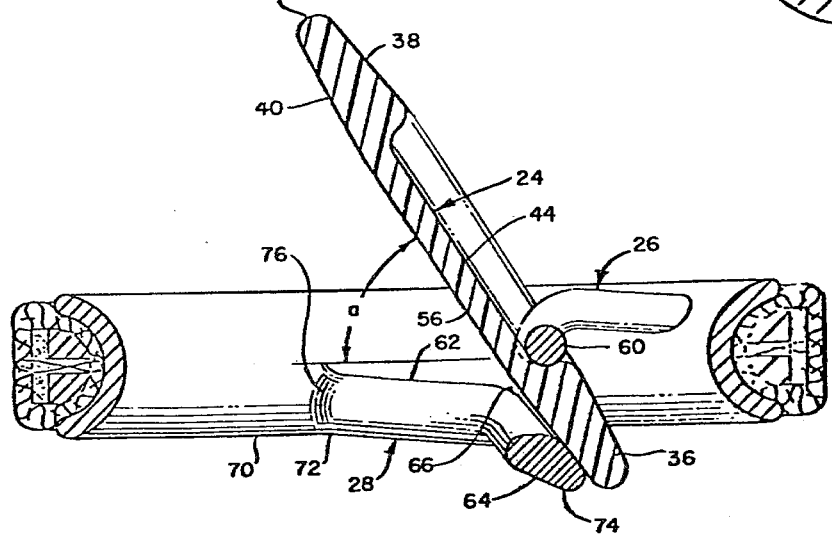
FIG. 5

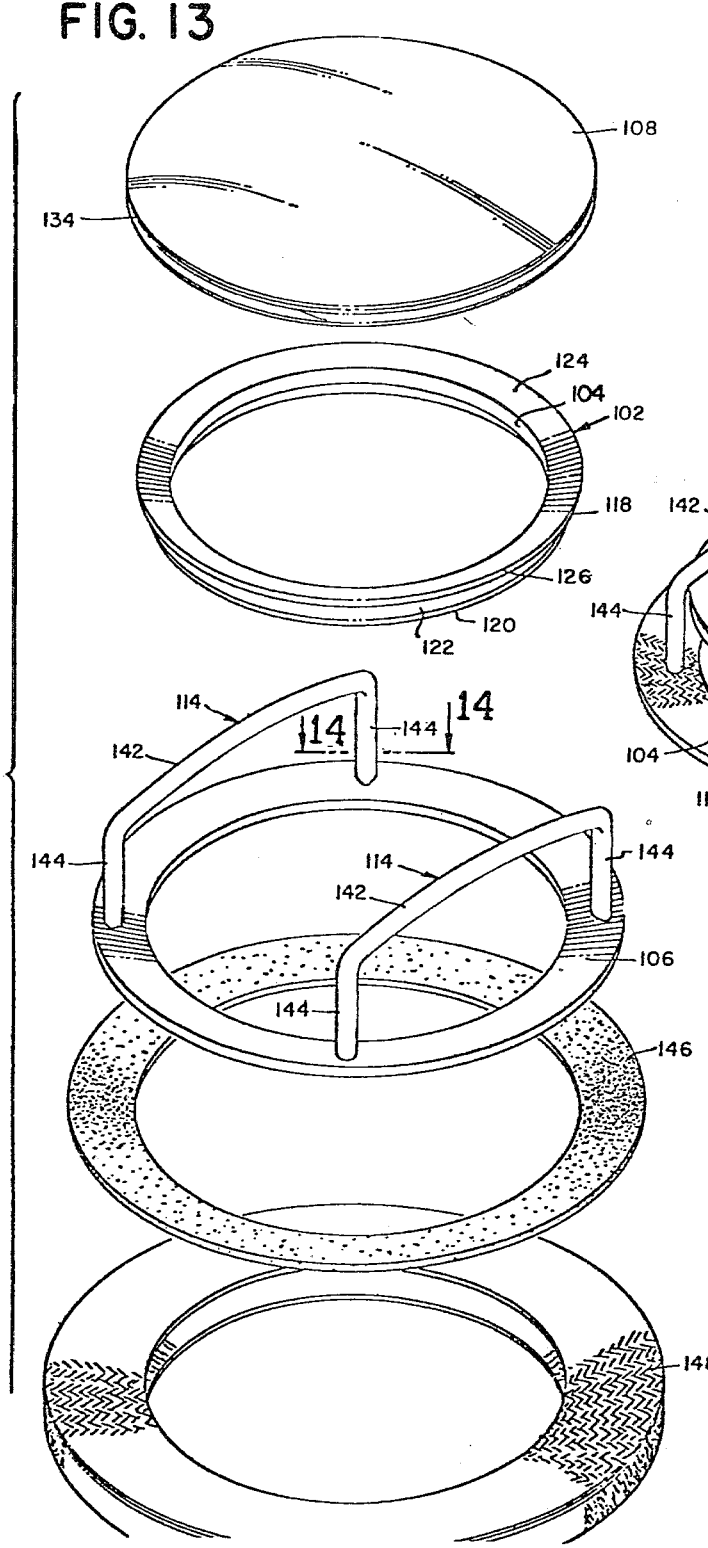
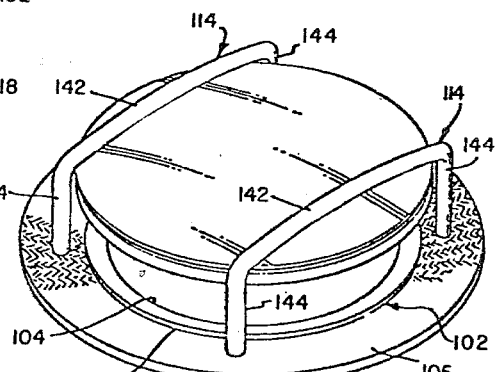
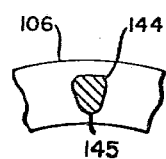
FIG. 13
FIG. 12
FIG. 14

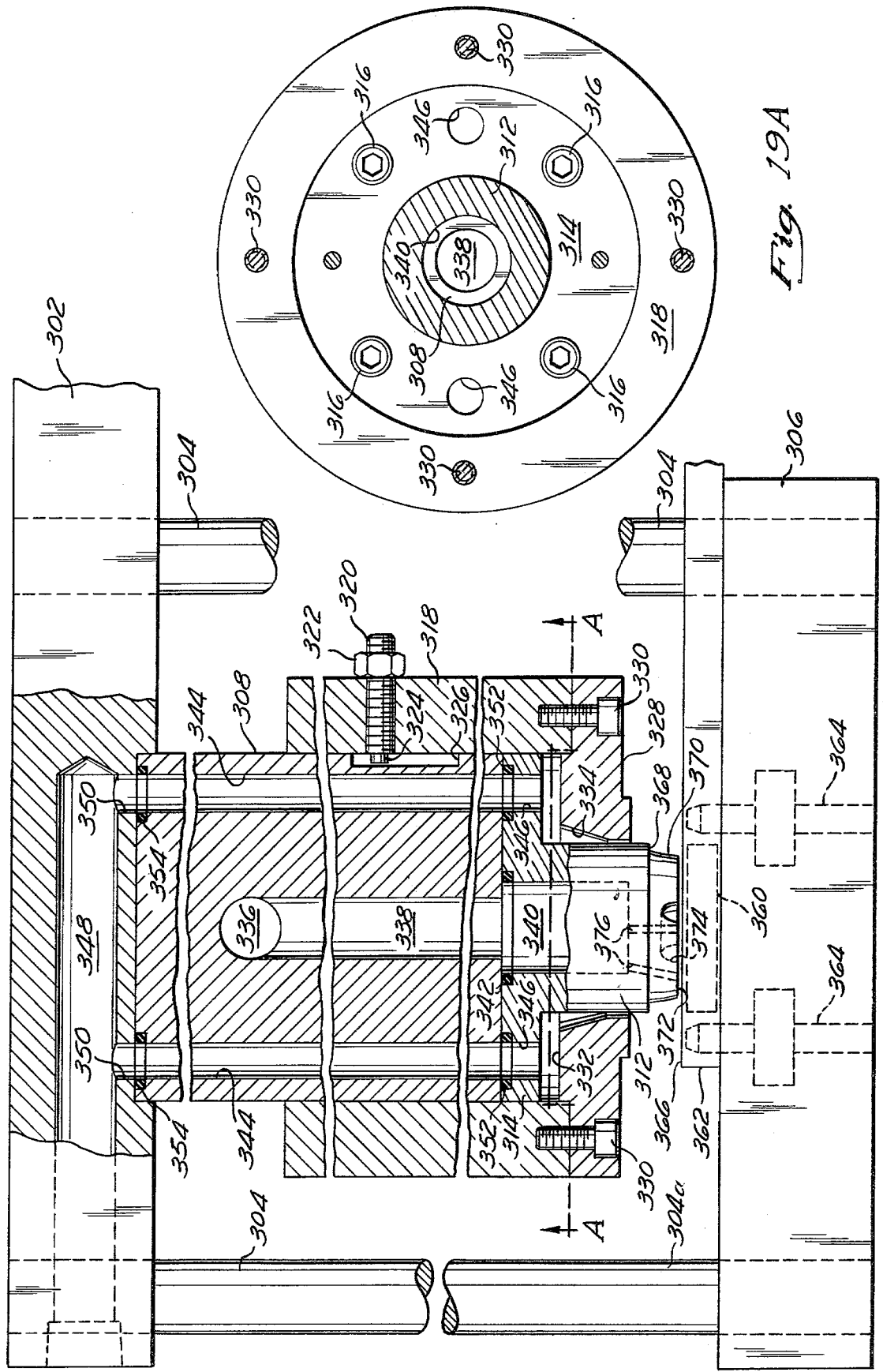

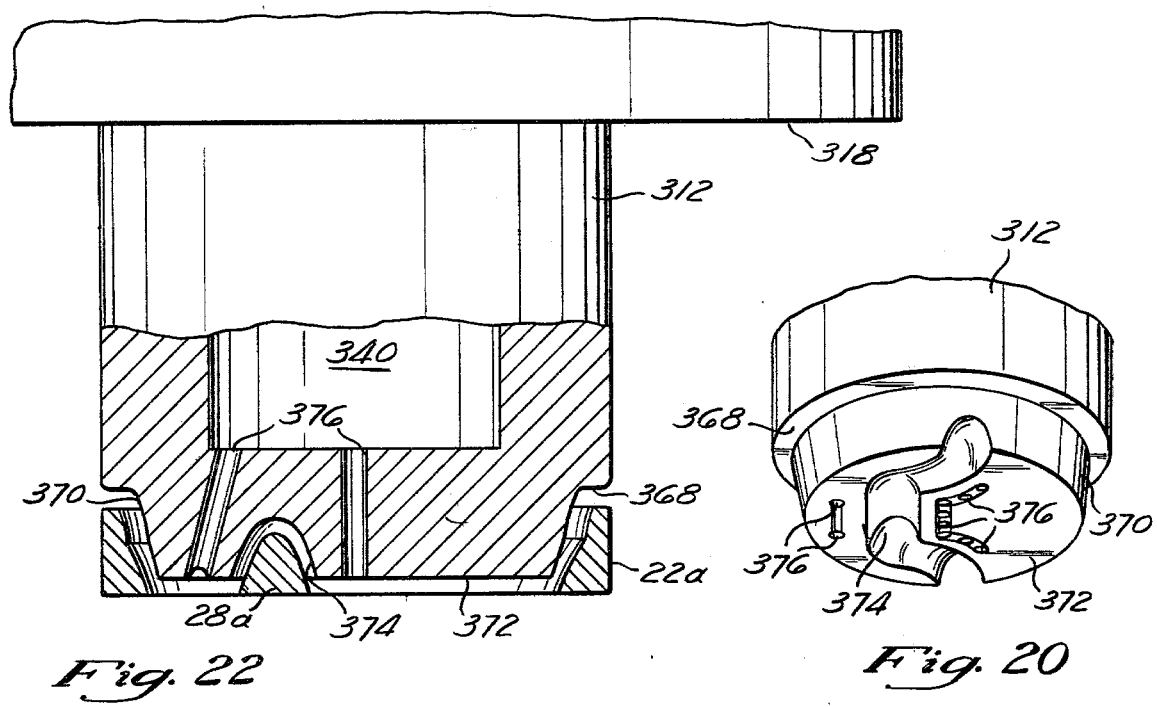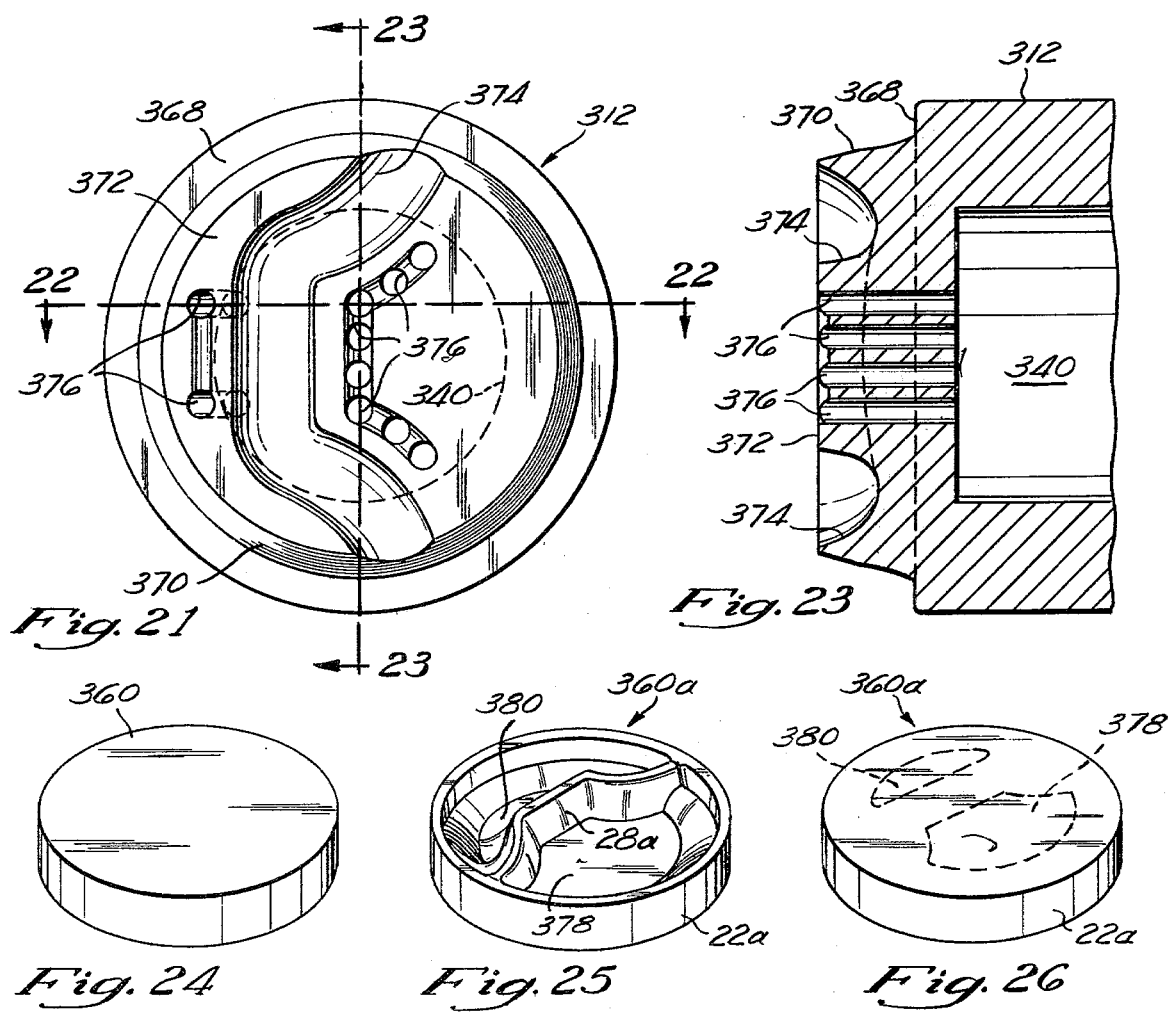

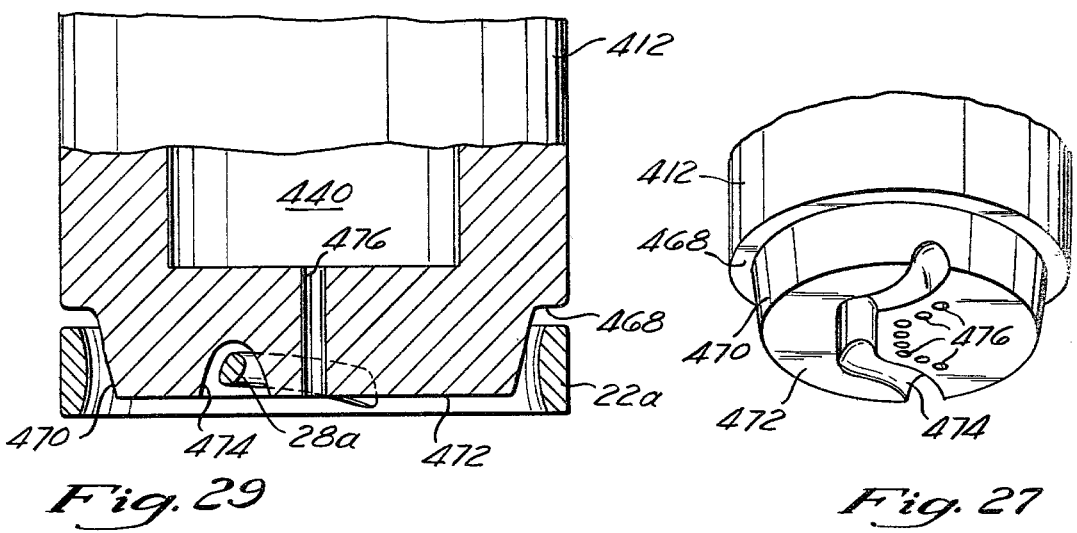
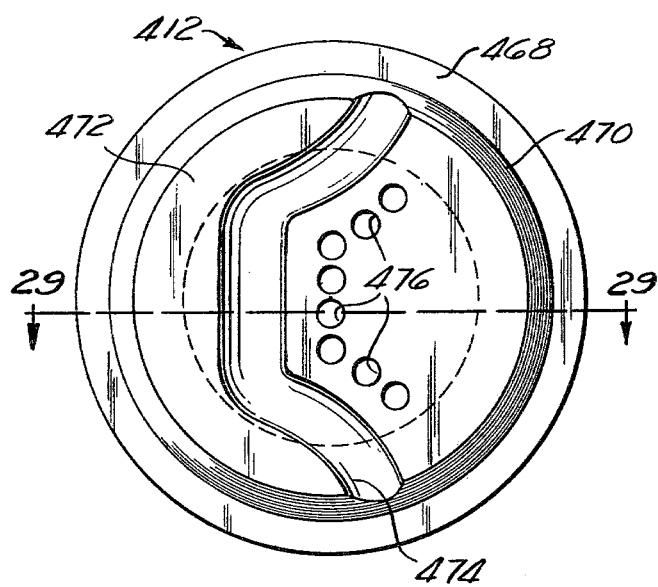
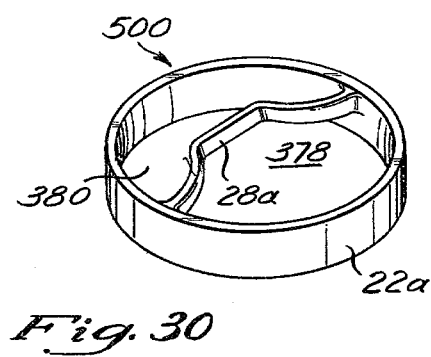

ELECTRO-CHEMICALLY MACHINED RING AND STRUT STRUCTURE FOR PROSTHETIC HEART VALVES

CROSS REFERENCE TO RELATED APPLICATION

This application is a Continuation-in-part of copending application Ser. No. 870,685, filed Jan. 19, 1978 and now abandoned.

BACKGROUND OF THE DISCLOSURE

Since the early 1960s, artificial heart valve prostheses have enjoyed tremendous success. Reliability and sustained high performance has been achieved by the use of very hard and exotic materials to form the structure. Such heart valve prostheses are exemplified in the following U.S. Pat. Nos. 3,534,411-Shiley; 3,812,542-Shiley; 3,824,629-Shiley; 4,057,857-Fettel, and the disclosures of these patents are incorporated herein by reference. Typically, such heart valve prostheses have a ring structure. Attached to the ring structure is usually some form of strut or pendant structure of elongated shape which supports the opening and closing of a discoid occluder. This occluder is disposed over the ring structure and substantially seals the orifice defined by the ring structure. In the art of heart valve prostheses, a constant search for improvement of the valve has continued since the early 1960s. The goals for such a search have been the reduction of thrombus formation in the heart within the vicinity of the heart valve through the reduction of stasis in blood flow (which stasis is roughly proportional to the size of the obstruction to blood flow presented by the heart), and concurrent with this goal, the goal of increasing the structural integrity of the heart valve. However, it has seemed that these two goals were incompatible in that increasing the structural integrity of the valve involved increasing the size of the structural members associated with the valve. Such an increase in size presents a greater obstruction presented to the blood flow with a concurrent increase in stasis, which thus increases the potential for thrombus formation. Thus, the search has continued for a method for improvement which would reconcile the two seemingly competing and irreconcilable goals of structural improvement and blood flow improvement.

Typically, in the prior art, the pendant structures or struts, attached to the valve ring, are formed of very hard metal wire, such as Haynes 25 material or a cobalt alloy, which is cut and welded to the ring structure after being shaped to the appropriate shape. Such welding necessarily results in the formation of a weld fillet extending beyond the welded juncture between the strut and the ring which has to be accommodated on the surface of the valve ring. Furthermore, these wire struts have a circular cross-section over which the blood has to flow. Although a circular cross-section for an obstruction sitting across the blood flow is not the most favorable cross-section for maximizing the flow across the valve, attempts to modify the circular cross-sectional configuration of the wire strut were generally unsuccessful because the machining of such a hard metal elongated wire strut leads to overheating of the wire and consequent distortion of the wire. These effects are due to the hard metal from which the wire must be formed and the prolonged machining time required to shape such a wire.

The prior art generally taught against integral formation of the strut and the valve ring in heart valves. The use of very hard metallic alloys, such as Haynes 25 material, or various alloys of cobalt, made the machining of such metal extremely difficult. The intricate shape of the strut necessary to permit the wobbly tilting action disclosed in the Fettel patent, U.S. Pat. No. 4,057,857, and the unique rocking occluder action also disclosed in that patent, made the machining of the strut even more difficult and seemingly impossible. The cross-sectional area of the strut is thin compared to its length, and this was a further obstruction in the machining of such a strut. It was found, for example, when the integral formation of the strut and ring was attempted through numerical control machining of a disc-shaped blank, the small size and intricate shape of the strut caused overheating and distortion in the strut because of the low heat conductive characteristics of the thin strut and because of the lengthy machining time necessary to achieve the intricate shape required for the strut. In stamping, it was found that the edge finish of the strut was not acceptable and the teardrop shape could not be sheared properly. When forging was attempted to form the integral strut and ring structure from a disc blank, the surface finish was bad as a result of the forging process and the costs in machining the finish after forging were prohibitive. Investment casting was also attempted in order to form the strut integral with the valve ring. However, such casting resulted in a porous surface finish which again resulted in the requirement for additional costly machining in order to obtain a good surface finish. As is well known in the art, a smooth surface finish is necessary in order for the heart valve prosthesis to work successfully. Also, the formation of voids within the structure by casting presented a serious risk. Laser machining was also attempted to form the strut and ring integral with one another from a disc blank. However, the teardrop shape of the strut could not be formed with laser machining and the inside ring radius could not be formed. Because of the tight dimensional tolerances inherent in the heart valve design, electrical discharge machining was found to be impractical because dimensional control in such machining is difficult due to erosion of metal from the electrode of the tool. Furthermore, the outer periphery of the ring could not be formed using electrical discharge machining. Finally, in the effort to form the strut and the valve ring to be integral with one another, chemical milling was attempted. However, because of the slow etch rate of the hard material from which the valve ring and strut must be formed, the mask used in the chemical milling was unavoidably undercut in the attempt, and the shape of the resulting structure was distorted. Thus, it seemed apparent in the prior art that integral formation of the strut and ring was not a viable or practical solution to the problem of improving the structural integrity of the valve structure and improving the blood flow across the valve. Increasing the size of the cross-sectional area of the wire, while leading increased structural integrity to the juncture between the wire strut and the valve ring, unavoidably increases the pressure gradient across the valve by offering a larger obstruction to the blood flow through the orifice defined by the ring.

As an alternative method, the machining of a disc-shape blank to form a valve ring integral with a strut in a single integral structure has met with similar difficulties, discussed below. Furthermore, the advantages to be gained by integral formation of the strut and ring have not been fully appreciated in the teachings of the prior art.

SUMMARY OF THE INVENTION

In this invention the integral formation of the valve ring and discoid supporting strut is taught. Such integral formation is made possible by the process of electrochemical machining. Such integral formation of the ring and the strut enables the strut to be configured in teardrop cross-section which substantially improves the fluid-dynamic characteristics of the valve, thereby improving blood flow through the valve, since this shape offers substantially less fluid-dynamic resistance to blood flowing around the strut. This, in turn, permits the cross-sectional area of the strut to be increased without detracting from the favorable fluid-dynamic characteristics of the valve. The increase in cross-sectional area of the strut, in turn, increases the strength of the juncture between the strut and the ring, since increasing the cross-sectional area of the strut increases the amount of metal supporting the juncture between the strut and the ring. Thus, the goal of improving structural integrity of the valve and the goal of improving th blood flow through the valve in order to reduce thrombus buildup have both been achieved by the implementation of this invention.

In the incorporation of this invention as an improvement in the pivoted discoid heart valves as taught and claimed in U.S. Pat. Nos. 3,824,629 and 4,057,857, the closing support strut is formed integrally with the ring and given a teardrop cross-section. The closing support strut is chosen as opposed to the opening support strut in this type of valve because the closing support strut is larger and is more important in its effects on blood flow and structural integrity of the valve. However, if desired, the opening support strut can also be formed in the same manner as the closing support strut.

In the incorporation of this invention as an improvement in the center post heart valve, as taught and claimed in U.S. Pat. No. 3,812,542, the cantilevered support strut of the center post which lies across the flow field of the blood is chosen to be formed integrally with the valve ring and to be given the teardrop shape. Similarly, in the heart valve having a pair of parallel cage struts which are symmetrically disposed to one another, as taught and claimed in U.S. Pat. No. 3,534,411, the vertical portions of these struts which lie across the blood flow opening of the valve are chosen to be formed integrally with the valve ring and are given the teardrop-shaped cross-sectional configuration.

With respect to the pivoted discoid heart valves, the use of this invention as an improvement results in a two-fold improvement of the characteristics of the valve. As in all applications of this invention to the typical heart valve, the strength of the juncture between the strut and the valve ring is improved due to the increased cross-sectional area of the strut, and the fluid flow around the strut is improved by the introduction of the teardrop cross-sectional shape of the strut. In addition to these improvements, the required height of the ring is further reduced because the weld fillet, which necessarily extends beyond the juncture between the strut and the ring, is eliminated by the integral formation of the strut and the ring. Thus, the height of the ring need not be great enough to accommodate the extending weld fillet, and may be reduced by the width of the weld fillet which has been eliminated, thereby locating the valve ring edge flush with the junction between the strut and the valve ring. This reduced height of the valve ring reduces the amount of obstruction presented to the blood flow across the orifice defined by the ring, thereby improving flow characteristics and reducing stasis in the blood flow and formation of thrombus in the vicinity of the ring. Conversely, because the minimum height requirement of the ring has been reduced, the cross-sectional area of the strut may be increased without necessarily increasing the height of the ring.

In summary, with respect to pivoted discoid heart valves, this invention permits the strengthening of the juncture between the closing support strut and the valve ring and the improvement of the blood flow characteristics through the orifice of the valve by integral formation of the closing support strut with the valve ring. This integral formation permits the machining of the strut to a teardrop shape and eliminates the weld fillet at the juncture between the strut and the valve ring. Thus, increasing the cross-sectional area of the strut does not present a greater obstruction to the blood flow in the vicinity of the strut because the introduction of the teardrop shape reduces the fluid dynamic resistance presented by the strut. Also, the increase in the size of the cross-sectional area of the strut does not present an increased obstruction to blood flow in the vicinity of the ring because the elimination of the weld fillet reduces the minimum height requirement of the ring. In fact, by the introduction of the teardrop cross-sectional shape of the strut, and by the minimization of the required height of the ring through the elimination of the weld fillet, the blood flow through the orifice of the valve is substantially improved.

The integral formation of the strut with the ring has been made possible through this invention by the electrochemical machining of the valve. Electrochemical machining involves holding the workpiece, such as the disc-shaped blank, from which the heart valve is to be formed, close to a negative electrode or cathode, specifically within about 0.010 inches. The workpiece is charged positively and an electrolytic solution is forced, under high pressure, approximately 175 psi, in between the workpiece and the negative electrode. A high current density, of approximately 1000 amperes per square inch of machined area, is passed through the electrolytic solution between the negative electrode and the positively charged workpiece. Metallic ions are removed from the workpiece and placed into the electrolyte solution and thereby kept from forming on the cathode and distorting the cathode. The machining is rapid due to the high current density between the workpiece and the cathode. As applied to the heart valve, and in particular as applied to the pivoted discoid heart valve or the heart valve with arcuate occluder, the cathode takes the form of a die from which an enlarged heart valve structural could nearly be cast. The workpiece initially is a disc-shaped blank, the diameter of which is slightly larger than the outside diameter of the heart valve ring and the thickness of which is slightly greater than the height of the ring of the heart valve. While in the electrolytic solution and during the electrochemical machining, the cathode is fed down onto the workpiece, and a valve ring and closing support strut are formed by the removal of metal from the blank due to the current flow of metal ions from the blank into the electrolytic solution. The teardrop shape and the intricate structure of the closing support strut are successfully formed by the electrochemical machining process. The overheating or distortion of the strut prevalent in the prior art is eliminated through electrochemical machining, and the dimensional tolerances are tightly held in this machining process.

For a more thorough understanding of this invention, reference may be had to the following detailed description and drawings wherein:

FIG. 3 is a cross-sectional view taken along line 3—3 of FIG. 2;

FIG. 4 is a diagramatic cross-sectional view of the heart valve prosthesis of FIG. 3 taken substantially along curved line 4—4 of FIG. 2;

FIG. 5 is a cross-sectional view of the heart valve prosthesis taken along line 5—5 of FIG. 2 but showing the valve occluder in an opened position;

FIG. 12 is a top perspective view of a heart valve prosthesis with parallel cage struts constructed in accordance with this invention;

FIG. 13 is an exploded view of the heart valve prosthesis of FIG. 12;

FIG. 14 is a cross-sectional view of one of the parallel cage struts of FIG. 13, taken along line 14—14 of FIG. 13;

FIG. 19 is a cutaway cross-sectional view of the electrochemical machine tooling assembly used to form the heart valve with arcuate occluder illustrated in FIGS. 6, 7, 8, 9, 10, and 11;

FIG. 19A is a cross-sectional view taken along line A—A of FIG. 19;

FIG. 20 is a detailed bottom perspective view of the electrode used to form the proximal side of the valve structure;

FIG. 21 is a bottom plan view of the electrode of FIG. 20;

FIG. 22 is a cross-sectional view of the electrode of FIG. 21 taken along line 22—22 of FIG. 21 showing the electrode fitting over the proximal side of the valve structure being formed;

FIG. 23 is a cross-sectional view of the electrode of FIG. 21 taken along line 23—23 of FIG. 21;

FIG. 24 is a top perspective view of a blank used to form the valve structure;

FIG. 25 is a top perspective view of the completed proximal side of the valve structure after the electrochemical process using the electrode of FIGS. 20 through 23 has been completed;

FIG. 26 is a bottom perspective view of the structure of FIG. 25;

FIG. 27 is a bottom perspective view of the electrode used to form the distal side of the valve structure;

FIG. 28 is a bottom plan view of the electrode of FIG. 27;

FIG. 29 is a cross-sectional view of the electrode of FIG. 28 taken along line 29—29 of FIG. 28 showing the electrode fitting over the distal side of the valve structure being formed; and FIG. 30 is a top perspective view of the completed valve ring and strut structure.

DETAILED DESCRIPTION OF THE INVENTION

Figure 1:
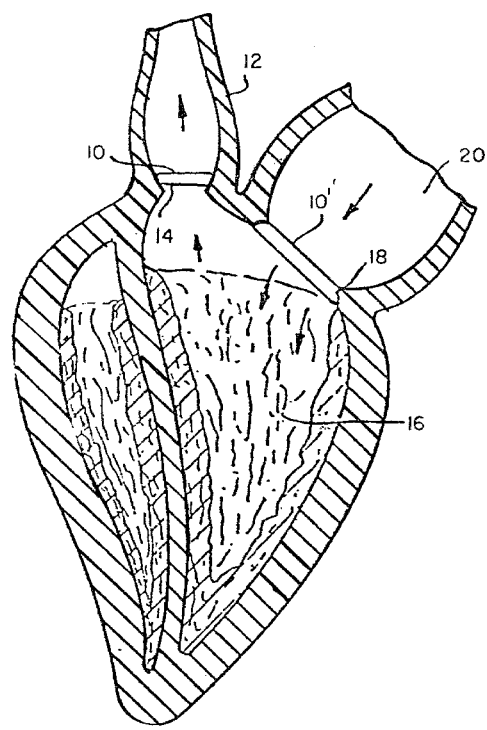
FIG. 1 is a diagramatic sectional view of a heart with the prosthesis of this invention inserted in place of the natural mitral and aortic heart valves.

FIG. 1 is illustrated of the general concept of heart valve prosthesis in which an artificial heart valve is implanted in place of a removed natural heart valve. The aortic and mitral valve prostheses are illustrated at 10 and 10' respectively. The aortic artery is illustrated at 12. The natural valve ring is illustrated at 14. The artificial heart valve 10 sits on the natural valve ring for an aortic heart valve prosthesis, for example. For the mitral heart valve prosthesis, the artificial heart valve 10' sits on the natural valve ring muscle tissue indicated at 18 at the left atrium 20. The distal side of the valve is defined to be the outlet or downstream side of the valve, while the proximal side of the valve is defined to be the inlet or upstream side of the valve. As is apparent from FIG. 1, the size of the valve varies depending upon the type of prosthesis for which it is designed.

DESCRIPTION OF THE FIRST EMBODIMENT

Figure 2:
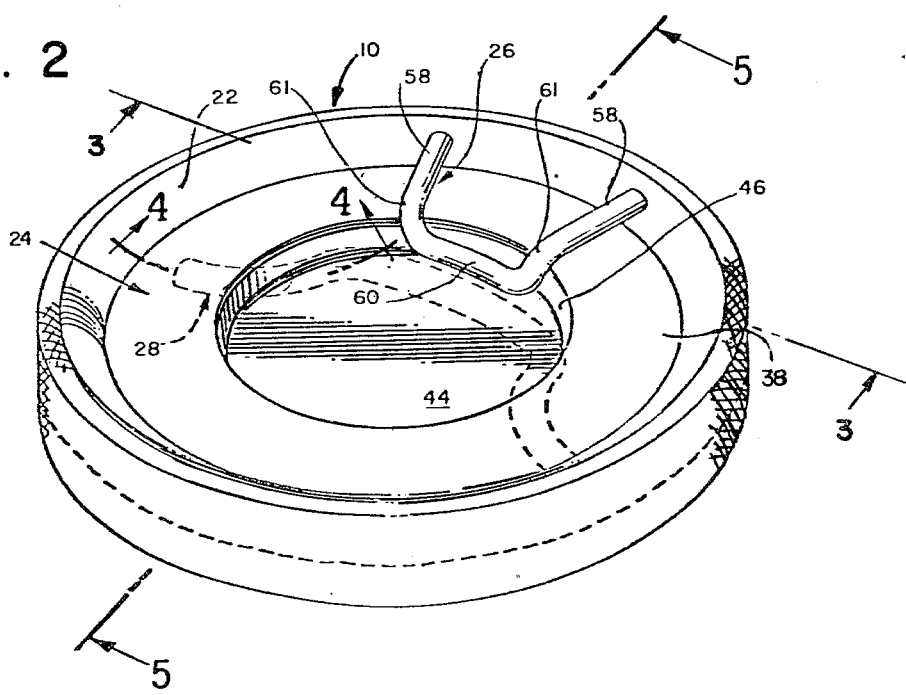
FIG. 2 is a top perspective view of the pivoted discoid heart valve prosthesis constructed in accordance with this invention.

In the first embodiment of this invention, the closing support strut of the pivoted discoid heart valve, as disclosed and claimed in U.S. Pat. No. 3,824,629-Shiley, is formed to be integral with the ring structure of that valve. From this description, it will become apparent that the full advantages for which this invention was intended are realized, namely that the flow of blood is improved because of favorable fluid-dynamic characteristics of the valve, the size of the valve is substantially reduced, and the structural integrity of the valve structure is improved. FIG. 2 shows a top perspective view of the pivoted discoid heart valve corresponding to the aortic heart valve prosthesis indicated in FIG. 1 at 10. The circular valve ring structure or body is indicated at 22 and it defines the orifice through which the blood must flow to enter the aortic artery. The valve occluder 24 is shown in FIG. 2 in the closed position. This view shows the distal side of the valve occluder 24. The valve occluder 24 is generally in a disc or discoid shape. The term discoid is used here to denote any geometric shape which is basically cylindrical in shape and in which the heighth of the cylinder is small in comparison with the diameter of the cylinder. The distal surface of the valve occluder 24 is divided into two regions; namely, an outer annular region, designated at 38 in FIG. 2, and a depressed, circular inner area, designated at 44. This inner despression fits the opening support strut 26 within the depressed area 44. The opening support strut 26 is comprised of two diverging strut elements 58, symmetrically disposed as a pair and attached to the valve ring 22. Integral with the pair of diverging strut elements 58 are a pair of shoulders 61 curving inwardly toward one another and merging into a base 60 which contacts the wall 64 of the depressed area 44. The closing support strut 28 is indicated by dashed lines as being disposed on the proximal side of the valve occluder 24.

FIG. 3 is a cross-sectional view taken along line 3—3 of FIG. 2 in which the closing support strut 28 is fully illustrated along with the shape of the discoid occluder 24. The relative thickness of the outer annular portion 38 and the relative thinness of the depressed inner area 44 of the discoid occluder 24 are apparent in FIG. 3. The base or middle portion 60 of the opening support strut is illustrated as impinging on the distal surface of the depressed area 44 of the occluder 24. The closing support strut 28 includes a pair of strut elements 62 forming the two junctures with the valve ring diverging inwardly of the ring 22 into a pair or proximally extending smooth curved shoulders 66. These smooth curved shoulders 66 merge into a middle portion 64 of the closing support strut 28, and the middle portion 64 curves proximally away from the valve ring 22.

FIG. 4 shows the distal surface 36 of the valve occluder 24 and the proximal surface 40 which sits on the proximally extending curved shoulder 66 of the closing support strut 62. The action of the rotation of the valve occluder 24 is indicated in the phantom outline of the occluder in FIG. 4 in which the pivot point is moved due to the rotation of the valve occluder 24.

FIG. 5 illustrates the heart valve of FIG. 3 in which the vane or discoid occluder 24 is in the opened position.

A significant feature of this invention is that the integral formation of the closing support strut 28 with valve ring 22 eliminates the weld fillet between the valve ring and the closing support strut. As a result, the lower or proximal edge 70 of the valve ring 22 is enabled to be flush with the lower edge or proximal edge 72 of the valve ring 22, as illustrated in FIGS. 3 and 5. Making reference now to U.S. Pat. No. 3,824,629, and in particular, FIGS. 5 and 6 of that patent, it may be seen that in the prior art the ring extended below the proximal edge of the closing support strut. This extra extension of the ring was necessary in order to accommodate the weld fillet which extended beyond the juncture between the ring and the closing support strut. With the integral formation of the closing support strut and the valve ring as accomplished by the present invention, the weld fillet has been eliminated and along with it the requirement for the extension of the ring beyond the lower edge 72 of the closing support strut 28. In this way, the cross-sectional area of the closing support strut 28 may be increased without increasing the height of the ring 22.

Reducing the height of the ring 22 reduces the amount of obstruction presented to the blood flowing across the valve thereby increasing the favorable fluid dynamic characteristics of the valve. Also, increasing the cross-sectional area of the closing support strut 28 increases the strength of the juncture between the closing support strut 28 and the ring 22.

The integral formation of the closing support strut 28 with the valve ring 22 is achieved by electrochemical machining a discoid blank piece of metal, as described more fully below. This eliminates the necessity of using a wire to form the closing support strut 28, as exemplified in the prior art, U.S. Pat. No. 3,824,629. Therefore, the cross-sectional shape of the closing support strut 28 need not be circular but may be any shape which may be machined electrochemically. In particular, the shape illustrated in FIG. 5 for the cross-section 74 of the closing support strut 28 is shown to be a modified teardrop shape. This teardrop shape has favorable fluid-dynamic flow characteristics such that the resistance to blood flow around the strut is substantially reduced while, at the same time, the total cross-sectional area of the closing support strut may be increased. As discussed before, the prior art taught that increasing the thickness of the circular strut would inherently offer greater hydrodynamic resistance to the hemodynamic flow of the blood. However, with the teardrop cross-sectional shape of the closing support strut 28, the resistance to flow is actually decreased, even though the cross-sectional area of the closing support strut may be increased. Because the cross-sectional areas of both the closing support strut and the juncture 76 have been increased, the amount of metal which forms the juncture 76 between the valve ring 22 and the closing support strut 28 is substantially increased, thereby correspondingly increasing the structural integrity of the structure of the valve ring to a substantial degree. In addition, the flow characteristics of the valve are substantially improved. The incorporation of this invention as an improvement into the pivoted discoid heart valve reconciles the two competing goals long sought after in the art, namely, the goal of increasing the structural integrity of the structure, and the goal of improving the fluid dynamic characteristics of the valve so as to decreases tasis and thrombus formation in the vicinity of the valve.

Description of the Second Embodiment

Figure 6:
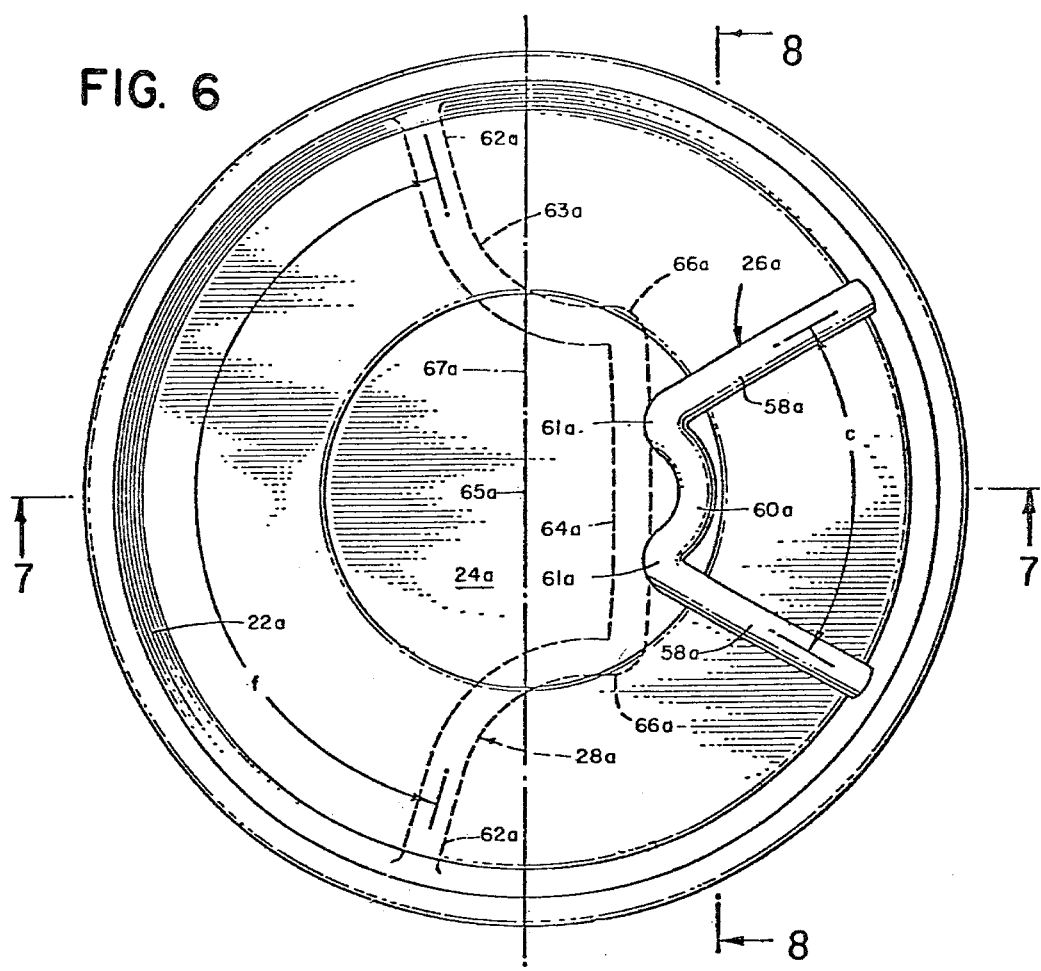
FIG. 6 is a top plan view of a pivoted discoid heart valve prosthesis having an arcuate occluder constructed in accordance with this invention.

FIG. 6 is a top plan view of a heart valve having an arcuate occluder as taught and claimed in U.S. Pat. No. 4,057,857, constructed in accordance with this invention, and showing a structure very similar to that of the pivoted discoid heart valve, previously discussed. The opening support strut is fully visible in FIG. 6 and designated generally at 26a. This strut consists of two inwardly disposed struts 58a forming a pair of rounded shoulders 61a with a middle portion 60a. The middle portion 60a abuts the wall of a central depression 44a in an arcuate occlunder 24a. The closing support strut is illustrated by the hidden lines and designated generally at 28a. The closing support strut 28a is disposed on the proximal side of the arcuate occluder 24a. The strut 28a is comprised of two inwardly extending support struts 62a merging into a pair of curved shoulders 63a passing through the axial center line 65a of the valve and formed through a pair of right-angles forming shoulders 66a which are formed on either side of a middle portion 64a.

The closing support strut 28a is formed integrally with a valve ring 22a. Therefore, the cross-sectional shape of the closing support strut 28a need not be circular. The closing support strut 28a and the valve ring 22a are preferably formed from a disc-shaped blank and electrochemically machined, as discussed below. Thus, the shape of the cross-sectional configuration of the closing support strut 28a may be selected from any shape which is fluid-dynamically favorable to flow through the orifice defined by the ring 22a. A modified teardrop cross-sectional shape 74a is illustrated as exemplary in FIG. 7, and is particularly suited to decreasing the hydrodynamic resistance to the flow around the closing support strut 28a.

Figures 9, 10:
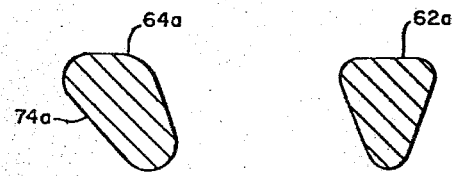
FIG. 9 is an enlarged cross-sectional view of the middle portion of the closing support strut of FIG. 8 taken along line 9—9 of FIG. 8.
FIG. 10 is an enlarged cross-sectional view of the outer portion of the closing support strut of FIG. 8 taken along line 10—10 of FIG. 8.
Figure 11:
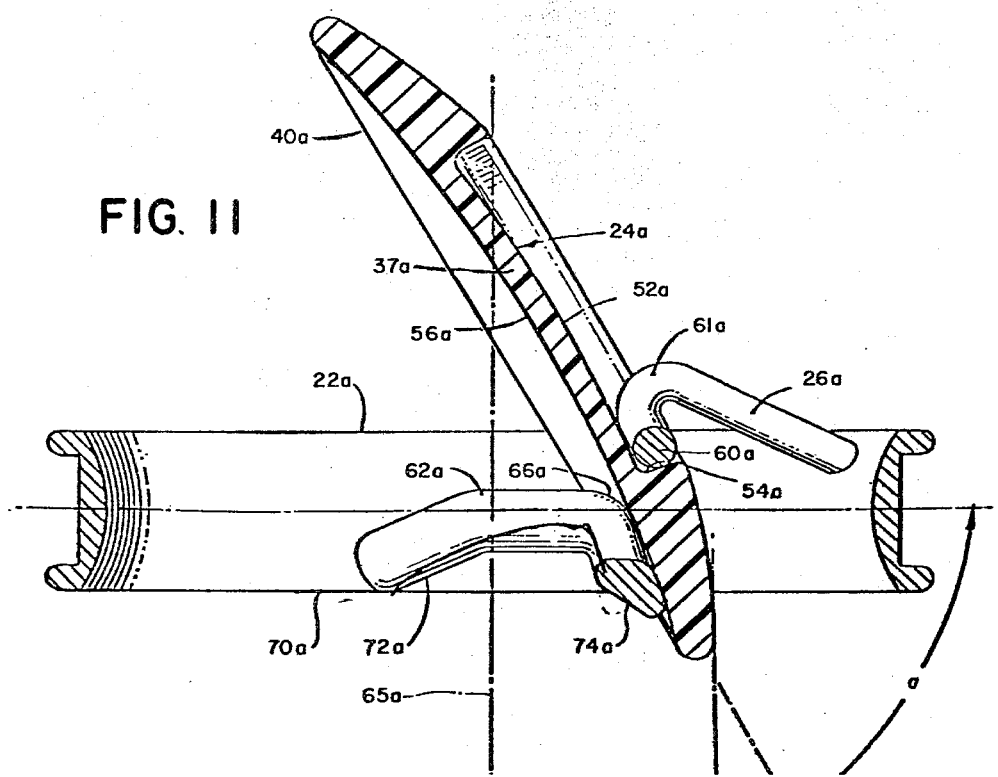
FIG. 11 is a cross-sectional view of the prosthesis similar to FIG. 7 but showing the valve occluder in an open position.
Figure 15:
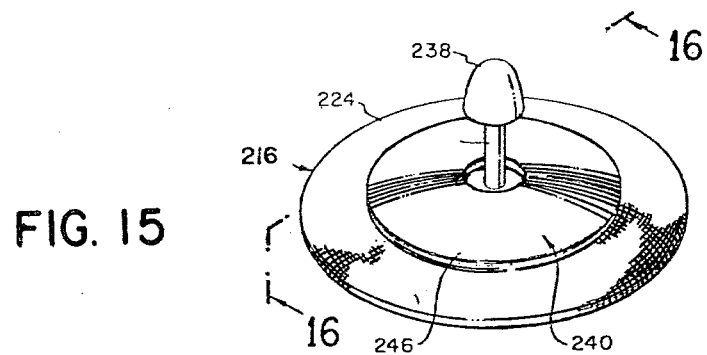
FIG. 15 is a top perspective view of a center post heart valve prosthesis constructed in accordance with this invention.
Figure 16:
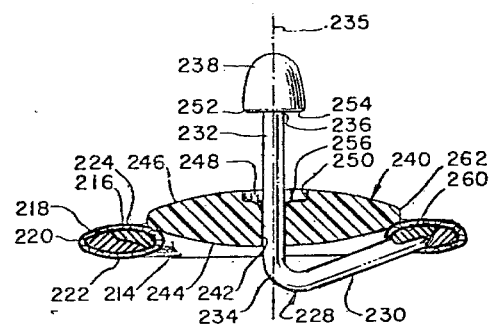
FIG. 16 is a cross-sectional view of the heart valve prosthesis of FIG. 15 taken along line 16—16 of FIG. 15.

FIGS. 9 and 11 show the cross-sectional shape 74a of the middle portion 64a of the closing support strut 28a. This shape illustrated is a modified teardrop shape designed to facilitate the valve closing action. Thus, the modified teardrop shape indicated at 74a is chosen to implement the rocking action discussed above and disclosed in U.S. Pat. Nos. 3,824,069 and 4,057,857 in which the pivot axis of the occluder changes as the occluder rotates between the open and closed position. Thus, the modified teardrop shape of the cross-sectional configuration of the middle portion 64 is chosen to be compatible with the feature of the changing pivot axis and the wobbly tilting action disclosed in U.S. Pat. No. 4,057,857. The modified teardrop shape indicated at 74a of the middle portion 64a of the closing support strut is further preferably chosen to permit the occluder to rotate to the open position defined by the angle a in FIG. 11.

The portion 62a of the closing support strut 28a have an equilateral teardrop shape cross-section as illustrated in FIG. 10. FIGS. 9 and 10 thus illustrate the complete flexibility in the choice of cross-sectional shapes made possible by the integral formation of the closing support strut with the valve ring taught by this invention. As illustrated, the cross-sectional shape need not be uniform across the entire closing support strut, but may vary across the length of the closing support strut for the purpose of maximizing fluid flow through the valve ring and minimizing the pressure gradient across the valve.

Figure 7:
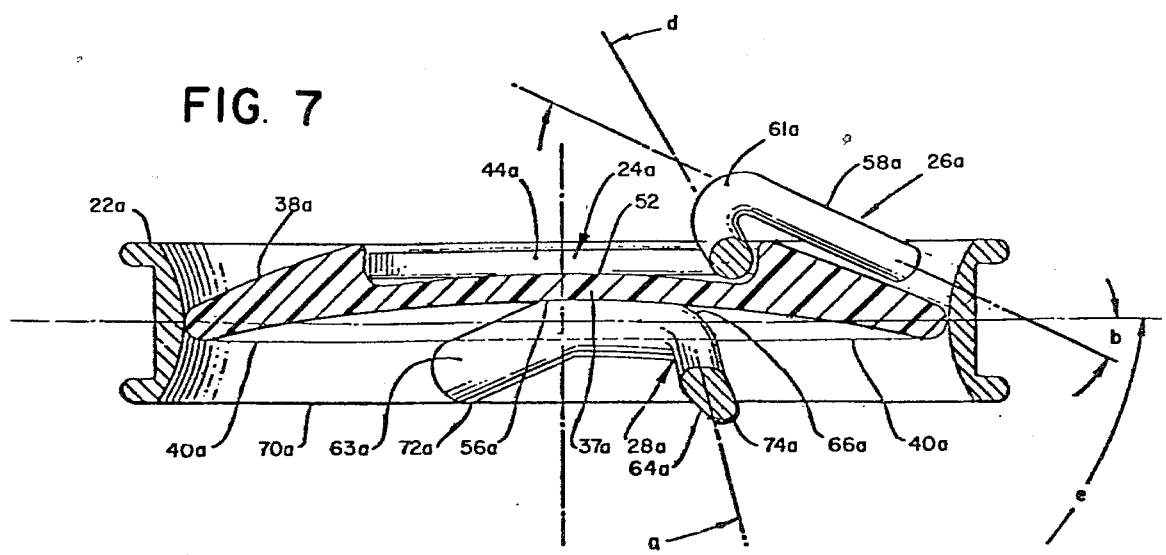
FIG. 7 is a cross-sectional view of the prosthesis of FIG. 6 taken along line 7—7 of FIG. 6.
Figure 8:
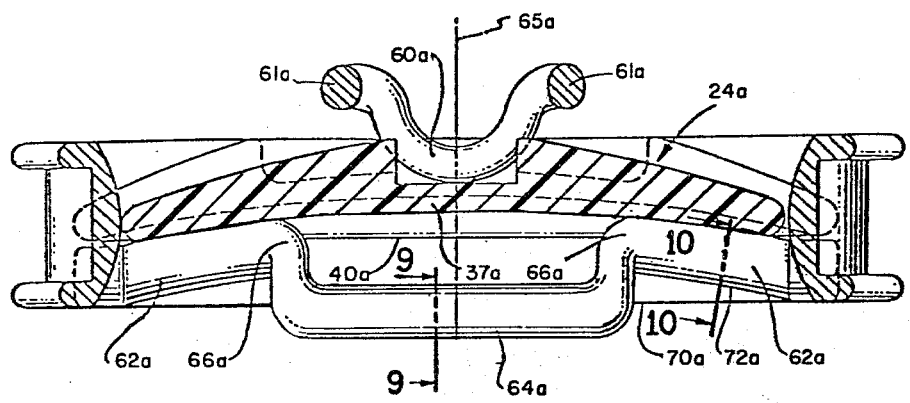
FIG. 8 is a cross-sectional view of the prosthesis of FIG. 6 taken along line 8—8 of FIG. 6.

The integral formation of the valve ring and the closing support strut also eliminates the need for a weld fillet at the juncture between the closing support strut and the valve ring. Thus, as shown in FIGS. 7, 8 and 11, the proximal or lower edge surface 70a of the valve ring and the proximal or lower edge surface 72a of the closing support strut 28a may be formed to be flush with one another.

The lower or proximal edge 70a of the ring and the lower proximal edge 72a of the closing support strut may be formed flush with one another because the weld fillet used in the prior art at the juncture between the valve ring and the closing support strut has been eliminated due to the integral formation of the ring and the closing support strut. In the prior art, it was necessary, in forming the heart valve with arcuate occluder, that the lower or proximal edge 70a of the valve ring extend below the lower or proximal edge 72a of the closing support strut 28a in order to accommodate the weld fillet which necessarily extended below the proximal edge 72a of the closing support strut 28a. With the elimination of this weld fillet, the thickness of the closing support strut may be increased and the height of the ring may be increased to such a point that the lower or proximal edge 70a of the ring and the lower or proximal edge 72a of the closing support strut are flush with one another and the ring does not extend below, or proximally of, the juncture between the valve ring and the closing support strut. This eliminates the amount of ring structure which is presented to the blood flow, and thereby improves the blood flow by decreasing the amount of obstruction presented thereto across the orifice defined by the valve ring 22a. Further, the aforementioned increase in the thickness of the closing support strut increases the structural integrity of the juncture between the closing support strut and the valve ring. This is due to the fact that an increase in the cross-sectional area of the closing support strut increases the amount of metal involved in forming the juncture between the valve ring and the closing support strut.

Again, the two competing goals long sought after in the art, namely, increasing the structural integrity of the valve and the goal of improving the fluid flow through the valve, have both been reconciled and fulfilled by the implementation of this invention as an improvement in the heart valve with arcuate occluder. The structural integrity has been increased because the thickness of the closing support strut has been increased, thereby strengthening the juncture between that strut and the valve ring. The fluid flow characteristics through the valve have been increased because the minimum height requirement of the valve has been decreased by the elimination of the weld fillet, and by the modified teardrop-shaped cross-sectional configuration of the closing support strut. All this has been made possible by the formation of the valve ring and closing support strut as an integral structure formed from a disc-shaped blank by the process of electrochemical machining.

Description of the Third Embodiment

Turning now to FIG. 12, a top perspective view of a parallel cage strut heart valve prosthesis is illustrated, corresponding to the aortic valve prosthesis illustrated in FIG. 1 at 10. FIG. 13 is an exploded view of this heart valve prosthesis and shows a ring 102 defining an orifice 104 which is sealed by a discoid occluder 108 which sits over the ring 102. As is apparent from FIG. 12, the movement of the discoid occluder 108 is restricted and bounded by a pair of parallel cage struts 114 which are supported on an annular retaining ring 106. The parallel cage struts 114 each comprise a pair of support legs 144 which extend vertically and perpendicularly from the annular retaining ring 106 and are joined together by a horizontal stop portion 142 which extends perpendicularly of the legs 144 and in general parallel relation to the plane defined by the outer perimeter of the circular annular retaining ring 106. The ring 102 is held within the inner annulus defined by the annular retaining ring 106 by means of an upper flange 118 and a lower flange 120 integral with the ring 102. For this purpose, a portion of the annulus of the annular retaining ring 106 fits inside an annular groove 122 between the upper flange 118 and lower flange 120 of the ring 102, thereby firmly holding the ring 102 within the annular retaining ring 106. The discoid occluder 108, when in the closed position, sits over the upper surface 124 of the ring 102. The discoid occluder 108 travels perpendicular to the plane defined by the outer circle of the annular retaining ring 106, and abuts the stop portion 142 of each of the support struts 114 in its full open position. After passing through the orifice defined by the ring 102, the blood must flow radially of the circular annular retaining ring 106 and around each of the legs 144. For this reason, the cross-sectional shape of the legs 144 determines the amount of fluid-dynamic resistance to blood flow through the valve and therefore determines the pressure gradient across the valve.

The use of an annular cloth pad 146 and an annular cloth sleeve 148 with the valve of FIG. 12 to provide aortic heart valve prosthesis 10 illustrated in FIG. 1 is disclosed and claimed in U.S. Pat. No. 3,534,411.

In the valve of FIG. 12, the pair of parallel cage struts 114 are formed integrally with the annular retaining ring 106. During the machining of the disc blank from which the annular retaining ring 106 and the integral parallel cage struts 114 is machined, a teardrop cross-sectional shape is advantageously formed in each parallel cage strut. FIG. 14 illustrates the disposition of such a teardrop cross-section in each of the legs 144 which substantially improves the fluid flow characteristics through the valve. An acutely arcuate vertex 145 of the teardrop shape is presented to the blood flow and, therefore, presents less fluid-dynamic resistance to the flow. This lowers the pressure gradient across the valve and improves the blood flow and washing action of the blood to minimize thrombus formation in the vicinity of the valve. Thus, due to the use of the teardrop cross-section in the leg 144, the cross-sectional area of the struts may be enlarged and thickened without impeding the flow of blood through the valve.

In summary, the improvement incorporated into the parallel cage strut heart valve consists in forming each of the parallel cage struts 114 integrally with the annular retaining ring 106, and integrally forming the parallel cage strut legs 144 to have a teardrop shape in which the acute vertex of the teardrop points opposite to the direction of the blood flow such that the vertex is presented to the blood flowing past the leg 144. The machining of the shape of the parallel cage strut, heretofore impossible because of heat loss and distortion due to the relatively long length and small thickness of the cage strut 114, is made possible by the electrochemical machining of the shape of the strut from a large disc-shaped blank from which the strut and the annular ring 106 are integrally formed.

Description of the Fourth Embodiment

Figure 17:
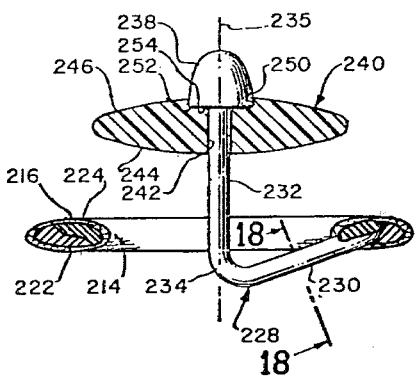
FIG. 17 is a view similar to FIG. 16 but showing the valve occluder in the open position.

FIGS. 15–18 illustrate this invention incorporated in a center post heart valve. This valve is the subject of U.S. Pat. No. 3,812,542. The center post heart valve may be used in the prosthesis as illustrated in FIG. 1 and indicated at 10. The valve is comprised of an annular retaining ring 216 which has a distal side 224 and a proximal side 222. The retaining ring 216 defines a blood flow orifice 214 through the center thereof. A frusto-conical discoid occluder 240 sits on the distal side 224 of the annular retaining ring 216 forming a seal for the orifice 214 on the distal side 224 of the ring 216. The movement of the occluder 240 is restrained by the L-shaped guide member or strut 228 which passes through a tight-fitting opening 242 in the occluder 240. The L-shaped guide member is comprised of a first leg 230 extending transversely from the retaining ring 216. A shoulder is formed at 234 in which the leg is merged into a center post portion 323 of the L-shaped strut 228. The opening 242 in the occluder 240 fits around the center post 232 in such a manner as to accurately guide the movement of the occluder up and down along the valve structure between the open and the closed position illustrated respectively in FIG. 17 and FIG. 16. At the distal end 236 of the center post 232 a stop knob 238 is disposed firmly and symmetrically with respect to the center axis 235 of the center post 232. When the occluder 240 is in the full opened position, as illustrated in FIG. 17, the bottom 254 and the perimeter 252 of the stop knob 238 are seated in a reces 248 in the distal surface 246 of the occluder 240 such that the stop knob perimeter 252 abuts against the perimeter 250 of the recess 248. The depth 256 of the recess 248 is sufficient to assure fluid damping of the stopping motion between the bottom surface 254 and the recess 248. When the occluder is in the closed position illustrated in FIG. 16, the proximal face 244 of the occluder 240 rests on distal surface 244 of the annular ring 216 to provide a seal which closes the valve.

In use as heart prosthesis, blood flows through the orifice 214 in a direction away from the proximal side 222 of the ring and towards the distal side 224 of the ring. From this it is apparent that the transverse leg portion 230 of the L-shaped guide member 228 acts as an obstruction around which the blood must flow. This obstruction is preferably minimized. In the prior art, exemplified in U.S. Pat. No. 3,812,542, the minimization of the obstruction presented by the leg 230 to the blood flow through the orifice is achieved by the minimization of the cross-sectional area of the leg 230. As taught by U.S. Pat. No. 3,812,542, the L-shaped member 228 is preferably formed by a single piece of wire having a constant diameter of approximately 1/16th of an inch. Because of the cantilever fashion of the attachment of the strut 228 to the ring, the juncture between the leg 230 and the ring 240 is critical for the structural integrity of the valve. Such structural integrity would be improved by any increase in the thickness of the wire at the leg portion 230. However, such an increase in thickness would correspondingly increase the amount of obstruction presented to the blood flowing through the orifice 214, and thereby increase the pressure gradient across the valve.

Figure 18:
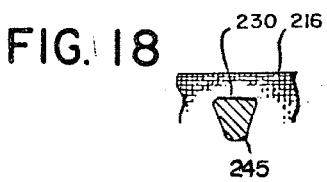
FIG. 18 is a cross-sectional view of the attachment leg of FIG. 17, taken along lines 18—18 of FIG. 17.

Contrary to the teaching of the prior art, in this invention the center post 232 and the cantilevered leg 230 are formed integrally with ring 214 from a single disc-shaped blank using the process of electrochemical machining. This permits a fine machining to be carried out on the shape of the cantilever support member. 228 to give it a teardrop cross-sectional configuration at the leg portion 230 which is disposed across the blood flow to the orifice. This cross-sectional shape is best illustrated in FIG. 18, which illustrates the preferred orientation of the teardrop cross-section of the strut 230 wherein an acutely arcuate vertex 245 of the teardrop is pointed into the oncoming blood flow.

According to the prior art, because the cantilevered support member 228 had been formed of wire, preferably welded to the annular support ring 214, any machining or changing in shape of the cross-sectional configuration of the strut would have resulted in overheating and distortion due to the long machining time required because of the hardness of the materials used to form the valve. According to this invention, the teardrop shape cross-section of the strut 230, illustrated in FIG. 18, decreases fluid-dynamic resistance to blood flow through the valve and thereby permits an increase in the cross-sectional area of the leg 230. This increase in cross-sectional area results in a stronger juncture between the ring 216 and the leg 230. This increase in structural integrity is due to the additional amount of metal within the juncture between the ring 216 and leg 230.

Electrochemical Machine Tooling Assembly

FIGS. 19 and 19A illustrate the electrochemical machine tooling assembly used in the electrochemical machining of an integrally formed valve ring and closing support strut, and particularly the strut 28a illustrated in FIGS. 6-11.

Referring first to FIG. 19, an electrode support 302 is moveably mounted for vertical translation on two alignment rods 304. The rods 304 are supported in a locating stationary base 306. An electrode mounting head 308 is suspended above the base 306 by the support 302. As shown in FIG. 19, a proximal side forming electrode or die 312 (which is more clearly illustrated in FIGS. 20-23, and which will be described in detail hereinafter) has an annular mounting flange 314 which seats against the underside of the mounting head 308. The electrode or die 312 is removably attached to the mounting head 308 by means of a plurality of bolts 316 (as illustrated in FIG. 19A) which pass through the mounting flange 314 into the head 308.

A sleeve 318 is mounted in a slideable engagement around the mounting head 308 by means of a set screw 320 and nut 322. The set screw 320 has a tip 324 which is accommodated by a recess 326 in the outer wall of the mounting head 308. The travel of the screw tip 322 within the recess 326 defines the limit of travel of the sleeve 318 with respect to the head 308. An annular collar or dam 328 is attached to the bottom of the sleeve 318 by means of a plurality of screws or bolts 330. The collar or dam 320 is configured so that a horizontal annular gap 332 is formed between the collar and the electrode mounting flange 314, which gap communicates with a vertical annular channel 334 formed between the collar 328 and the electrode 312.

An electrolytic solution outlet 336 is provided in the mounting head 308 and communicates through an outlet passage 338 with a cavity or chamber 340 formed in the electrode 312. The juncture between the cavity or chamber 340 and the passage 338 is advantageously sealed by means of an o-ring 342.

A pair of electrolytic solution inlet passages 344 are provided in the head 308. These passages 344 communicate with the annular gap 332 through a pair of ports 346 in the electrode flange 314. The upper ends of the passages 344 communicate with an inlet manifold 348 in the support 302 through a second pair of ports 350 in the support 302. The junctures between the passages 344 and the flange ports 346 are sealed by o-rings 352, and the junctures between the passages 344 and the support ports 350 are sealed by similar o-rings 354.

A disc-shaped blank 360 illustrated in FIG. 24 and indicated by dashed lines in FIG. 19 is held in place by a holding plate 362 which in turn is aligned by a pair of rotating pins 364 over the locating base 306. The holding plate 362 has a top surface 366 which is abutted by a peripheral rim 368 around the electrode 312 when the support 302 is moved down toward the base 306 to reach the bottom extent of its travel along the alignment rods 304 and 304a.

Referring now to FIGS. 20-23, the proximal side forming electrode 312 is shown in detail. As best seen in FIGS. 20, 22, and 23, extending downwardly from the rim 368 of the electrode 312 is a proximal side forming die face 370. The proximal side forming die face 370 has a bottom surface 372 which has a trough 374 for forming the proximal side of the strut 28a. As shown, the trough 374 conforms to the shape of the proximal side of the strut 28a and is sized somewhat larger than the strut so that as the strut is being formed, a clearance space of between 0.010 and 0.020 inches is maintained. A similar clearance space is maintained between the side of the die face 370 and the valve ring 22a as the latter member is being formed. Running through the die face 370 between the bottom surface 372 and the chamber or cavity 340 in the electrode 312 are a plurality of electrolytic fluid channels 376. These channels 376, which are advantageously located on both sides of the trough 374, provide for a complete circulation of the electrolytic fluid as will be presently described.

The formation of the proximal side of the valve structure proceeds as follows: A disc-shaped blank or workpiece 360 (FIG. 24) preferably of a metal such as Haynes-25 or a hard, corrosion resistant cobalt alloy, is retained in the holding plate 362. The height and diameter of the workpiece or blank 360 are slightly greater than the height and diameter respectively of the outside of the ring 22a of the heart valve prosthesis shown in FIGS. 6-11. The set screw 320 and nut 322 are loosened so that the sleeve 318 and collar 328 can be lowered until the bottom of the collar 328 comes into contact with the top surface 366 of the holding plate 362 and the set screw is then retightened to maintain the sleeve and collar in this position. An effective seal is thereby maintained around the electrode 312 between the collar 328 and the holding plate 362. However, the set screw 320 is not set so tightly as to prevent the vertical travel of the mounting head 308 within the sleeve 318.

The support 302 is lowered along the alignment rods 304 until the bottom surface 372 of the electrode 312 is brought to within approximately 0.010 inches from the workpiece 360. When the apparatus is so positioned, an electrolytic fluid (preferably a solution of approximately 1.25 pounds of sodium chloride per gallon of water) is pumped into the inlet manifold 348 at a pressure of approximately 175 pounds per square inch. The electrolytic fluid then descends through the passages 344, the annular gap 332, and the annular channel 334 into the narrow gap formed between the workpiece 360 and the bottom surface 372 of the electrode 312. The fluid fills the trough 374 and also flows upwardly through the channels 376 into the chamber 340 in the electrode, from which it flows upwardly through the outlet passage 338 and out of the outlet port 336 for recirculation by filtering and pumping means (not shown) back to the inlet manifold 348. A back pressure of approximately 40 pounds per square inch is maintained at the outlet port 336, thus providing a pressure differential of approximately 135 pounds per square inch between the inlet ports 350 and the outlet port 336. In this manner a constant high pressure, high velocity circulation of electrolytic fluid is maintained between the electrode and workpiece. Temperature regulating means (not shown) are incorporated into the electrolytic fluid circulation system to maintain the temperature of the fluid at approximately 105° F.

While the electrolytic fluid is circulating as described above, a positive electrical potential is applied to the workpiece 360 and a negative electrical potential is applied to the electrode 312, with the difference in potential between the electrode and workpiece being approximately 12 volts. This produces a current density of approximately 1000 amperes per square inch of machined area to pass between the electrode and the workpiece. This current flow causes metallic ions to be electrically removed from the proximal surface of the blank or workpiece 360 adjacent the bottom surface 372 of the electrode 312, and to pass into the electrolytic solution to be washed away through the flow of the fluid. This removal of metallic ions will result in an erosion of the workpiece, and in order to maintain the 0.010 inch gap between the workpiece and the electrode, the electrode must be lowered at a rate of approximately 0.110 inches per minute. As more and more metal is removed from the workpiece and as the electrode is gradually lowered, the proximal side of the strut 28a will take a shape conforming to the trough 374 as shown in FIG. 22. In a similar manner, the inner surface of the proximal side of the ring 22a takes a shape approximately conforming to the walls of the die face 270. As shown in FIGS. 25 and 26, the metal is almost completely eaten away by this process in the areas between the strut and the ring leaving a very thin layer of metal (approximately 0.0005 inches thick) in the area 378 and 380 which will be the major and minor orifices, respectively, of the finished valve.

When the formation of the proximal side of the valve structure is finished, the workpiece will have the form designated by the numeral 360a in FIG. 25 and 26. The proximal sides of the valve ring 22a and the strut 28a will be completely formed, nd the major and minor orifices 378 and 380, respectively will be partially formed. At this point in the process, the mounting head has been lowered to the point where the rim 368 of the electrode 312 has come into contact with the top surface 366 of the holding plate.

Preparation must now be made for the formation of the distal side of the valve structure. The flow of electrolytic fluid is shut off and the electric potentials are removed from the electrode and the workpiece. The mounting head 308 is raised along the alignment rods 304, carrying with it the electrode 312, the sleeve 318 and the collar 328. The collar 328 is removed by removing the screws or bolts 330 which, as previously mentioned, retain the collar on the sleeve 318. The proximal side forming electrode 312 is then removed by removing the bolts 316 shown in FIG. 19A. It is replaced with a distal side forming electrode 412, illustrated in FIGS. 27, 28 and 29. The collar 328 is then reattached to the sleeve 318. The thin metal layers in the areas 378 and 380 of the workpiece are manually removed with a sharp instrument, and the workpiece 360a is then flipped over and placed in the holding plate 362 so as to present the distal side (FIG. 26) in a confronting relationship with the electrode 412. The collar or dam 328 is then lowered into position against the top surface 366 of the holding plate 362 as previously described, and the formation of the distal side of the valve structure is ready to proceed in the same manner as in the formation of the proximal side.

Referring now to FIGS. 27, 28 and 29, the distal side forming electrode or die 412 is seen to resemble the proximal side forming electrode 312 in all respects except for the portion of the electrode in the area of the die face 470. Thus, when the distal side forming electrode 412 is mounted on the mounting head 308, the view taken along line A—A of FIG. 19 would be identical to that shown in FIG. 19A.

The die face 470 of the distal side forming electrode 412 is segregated from the body of the electrode by a peripheral rim 468 and has a bottom surface 472 having a trough 474 for forming the distal side of the strut 28a. Like the proximal side forming electrode 312, the distal side forming electrode 412 is provided with electrolytic fluid channels 476 communicating between the bottom surface 472 and an interior chamber of cavity 440. These channels 476 serve the same function as the channels 376 in the proximal side forming electrode 312.

As can be seen in FIG. 29, the trough 474 has a configuration corresponding to the shape of the distal side of the strut 28a, but is sized somewhat larger, for the purposes previously discussed. Thus, as the blank 360a is eroded by the electro-chemical machining process, the distal side of the strut 28a takes a shape conforming to that of the trough 474 while the distal side of the ring 22a takes a shape conforming to the walls of the die face 470. After the die has reached the bottom most point of its travel as previously described, the integral strut and ring structure takes on its final configuration, with the major and minor orifices 378 and 380, respectively, of the valve being completely formed between the strut and the ring. The final valve structure designated by the numeral 500 is illustrated in FIG. 30. As can be seen from FIG. 30, the strut and the ring are formed by this method as an integral unit, and if the troughs 374 and 474 are appropriately configured, the strut 28a will have the modified teardrop shape previously discussed. The structure 500 is now ready for a final machining by conventional means to provide the accurate sizing of the ring and to provide the circumferential groove shown in FIGS. 6, 7 and 11.

Although the advantages of electromechanically machining the opening support strut 26a are less pronounced, this can be accomplished, if desired, by providing an additional trough of appropriate configuration in each of the die faces 370 and 470.

Those of ordinary skill in the art of electochemical machining will recognize that to accommodate variations in the characteristics in metal of which the disc-shaped blanks 360 are formed, it may be necessary to adjust the operational parameters of the electrochemical machining process. Thus, in order consistently to achieve a satisfactory finish for the valve structure 500, it may be necessary to adjust the rate at which the electrochemical machining process takes place. This may be accomplished, for example, by varying the pressure differential in the electrolytic fluid circulation system so as to increase or decrease the rate of flow of electrolytic fluid across the workpiece. Alternatively, the electrical potential between the workpiece and the electrode may be varied to adjust the current density between the workpiece and the electrode, so as to maintain critical dimensions. Thus, the values for these various parameters which are given above in the description of the process, while having produced totally satisfactory results, are merely exemplary, in that it is within the abilities of those persons of ordinary skill in the art of electromechanical machining to find other values for these operational parameters which will yield satisfactory results for different conditions, requirements, and metal characteristics.

While the method and apparatus for producing the integral strut/ring structure have been described only in conjunction with the heart valve with arcuate occluder, (the embodiment of FIGS. 6–11), the use of this method and apparatus to formulate the integral ring/strut structures of the other prosthetic heart valve embodiments is disclosed above can be accomplished in an almost identical manner, with the only major change being in the configuration of the die faces of the electrodes. With the teachings of this disclosure, it would be within the abilities of those of ordinary skill in the art of electrochemical machining to provide appropriately configured electrodes for the formulation of valve structures for all of the valve embodiments disclosed herein, as well as other forms of heart valve prostheses which could make advantageous use of an integral strut/ring structure.

What is claimed is:

1. A method for making an integral ring and strut structure for a prosthetic heart valve having an occluder movably mounted in a ring by a strut, said method comprising the steps of:
   (1) placing a first side of a disc-shaped blank of hard, corrosion-resistant metal into close proximity with a first electrode having a first die face, said first die face being circular to form a ring of inside diameter approximately equal to the diameter of said first die face, and having a concavity for a strut which is integral with said ring;
   (2) flowing electrolytic fluid between said first die face and said blank while simultaneously applying an electric potential between said electrode and said blank to cause an electric current to flow therebetween, said current causing metallic ions to be carried from said blank into said fluid thereby eroding said blank in conformity with the configuration of said first die face;
   (3) continuing the flow of said fluid and the application of said electric potential until said blank is eroded to a shape corresponding to the configuration of a first side of said integral ring and strut structure;
   (4) placing a second side of said blank into close proximity with a second electrode having a second die face, said second die face being circular to form a ring of approximately equal diameter to that ring formed by said first die face, and having a concavity for a strut which is integral with said ring and is matched to the concavity in said first die face;
   (5) flowing electrolytic fluid between said second die face and said blank while simultaneously applying an electric potential between said electrode and said blank to cause an electric current to flow therebetween, said current causing metallic ions to be carried from said blank into said fluid, thereby eroding said blank in conformity with the configuration of said second die face; and
   (6) continuing the flow of said fluid and the application of said electric potential until said blank is eroded to a shape corresponding to the final configuration of said integral ring and strut structure.

2. An integral ring and strut structure for a prosthetic heart valve having an occluder moveably mounted in said ring by said strut, wherein said integral ring and strut structure is made by the method of claim 1.

3. The integral ring and strut structure of claim 2, wherein at least a portion of said strut has a cross-sectional shape substantially resembling a tear-drop.

4. A method for making an integral ring and strut structure for a prosthetic heart valve having an occluder moveably mounted in a ring by a strut, said method comprising the steps of:
   (1) electrochemically machining one side of a disc-shaped blank of hard, corrosion resistant metal using a first electrode having the configuration of a first die, said first die being circular to form a ring, and having a concavity to form a strut which is integral to said ring; and
   (2) electrochemically machining the other side of said blank using a second electrode having the configuration of a second die, said second die being circular to form a ring of approximately equal diameter to the ring formed by said first die, said second die having a concavity for a strut which is integral to said ring, and is matched to the concavity in said first die.

5. The integral ring and strut structure made by the method of claim 4.

6. The integral ring and strut structure of claim 5, wherein at least a portion of said strut has a non-circular cross-sectional shape which provides a low fluid dynamic flow resistance in proportion to cross-sectional area.

7. The integral ring and strut structure of claim 6, wherein at least a portion of said strut has a cross-sectional shape substantially resembling a tear-drop.

8. The integral ring and strut structure of claim 5, wherein said ring and strut structure comprises:
   a ring; and
   strut means for pivotally mounting a discoid occluder in said ring, said strut means being integral with said ring and extending across the interior thereof to provide a pivot for said occluder.

9. The integral ring and strut structure of claim 8, wherein said ring and said strut means each have an edge surface, said ring edge surface and said strut means edge surface being substantially flush with each other.

10. The integral ring and strut structure of claim 5, wherein said ring and strut structure comprises:
    a ring having a proximal side and a distal side; and
    strut means for moveably mounting a discoid occluder on the distal side of said ring, said strut means being integral with said ring and including a pair of parallel cage struts extending distally from and across said distal side of said ring to provide a stop for the movement of said occluder.

11. The integral ring and strut structure of claim 5, wherein said ring and strut structure comprises:
    a ring having a proximal side and a distal side; and
    strut means for moveably mounting a centrally apertured occluder on the distal side of said ring, said strut means being integral with said ring and comprising:
    a cantilevered leg portion extending radially from said ring inwardly into the interior thereof and toward said proximal side, and terminating in an arcuate bend toward said distal side; and
    a post portion extending axially through the interior of said ring from said bend to said distal side, said post portion providing means for confining the movement of said occluder by slidably engaging said occluder through said central aperture.

* * * * *